(12) United States Patent
Gudiño Casillas et al.

(10) Patent No.: US 12,178,923 B2
(45) Date of Patent: Dec. 31, 2024

(54) SYSTEM FOR CLEANING MODULAR BELTS

(71) Applicant: CLEVOT, S.A. DE C.V., Jalisco (MX)

(72) Inventors: Jorge Luis Gudiño Casillas, Jalisco (MX); Aldo Sainz Hernández, Jalisco (MX); Juan de Dios Vidrio Borrego, Jalisco (MX)

( * ) Notice: Subject to any disclaimer, the term of this patent is extended or adjusted under 35 U.S.C. 154(b) by 453 days.

(21) Appl. No.: 17/603,292

(22) PCT Filed: Apr. 17, 2019

(86) PCT No.: PCT/MX2019/000038
§ 371 (c)(1),
(2) Date: Oct. 12, 2021

(87) PCT Pub. No.: WO2020/209706
PCT Pub. Date: Oct. 15, 2020

(65) Prior Publication Data
US 2022/0184246 A1 Jun. 16, 2022

(30) Foreign Application Priority Data

Apr. 12, 2019 (MX) .................... MX/a/2019/004329

(51) Int. Cl.
*A61L 2/07* (2006.01)
*A61L 2/24* (2006.01)
(Continued)

(52) U.S. Cl.
CPC .................. *A61L 2/07* (2013.01); *A61L 2/24* (2013.01); *A61L 2/26* (2013.01); *B08B 1/12* (2024.01);
(Continued)

(58) Field of Classification Search
CPC ..... A61L 2/07; A61L 2/24; A61L 2/26; A61L 2/22; A61L 2202/17; B08B 1/165;
(Continued)

(56) References Cited

U.S. PATENT DOCUMENTS

| 4,960,200 A | 10/1990 | Pierce |
| 5,649,616 A | 7/1997 | Stecklow |

(Continued)

FOREIGN PATENT DOCUMENTS

| FR | 2725968 A1 | 4/1996 |
| FR | 3055891 A1 | 3/2018 |
| WO | WO-2017046165 A1 | 3/2017 |

*Primary Examiner* — Katina N. Henson
(74) *Attorney, Agent, or Firm* — Feeney IP Law; Alan F. Feeney

(57) ABSTRACT

The invention relates to a system for cleaning modular belts, characterized in that it comprises a support structure configured to be mounted and dismounted from the structure of a modular-belt conveyor, wherein a plurality of cleaning stations are mounted on the support structure, said cleaning stations consisting of: (a) a first surface cleaning station consisting of at least one roller with cleaning flaps disposed crosswise on the modular belt; (b) a cleaning preparation station consisting of at least one transverse duct disposed in an elevated manner with a plurality of ejection nozzles distributed along the length of the at least one duct and along the width of the modular belt in order to sprinkle water in the form of a spray directly on the modular belt; (c) a pre-cleaning station comprising a system of at least one self-adjustable plastic scraper; (d) a second surface cleaning station consisting of at least one pair of rollers with cleaning flaps, one being placed on the upper part of the modular belt and the other on the lower part thereof; (e) a deep-cleaning and sanitization station consisting of a system of rotary steam-spraying heads connected to a dry steam generator; and (f) a station for drying with warm air, formed by at least two air turbines with an elevated transverse diffuser.

11 Claims, 4 Drawing Sheets

(51) Int. Cl.
*A61L 2/26* (2006.01)
*B08B 1/12* (2024.01)
*B08B 1/14* (2024.01)
*B08B 1/16* (2024.01)
*B08B 1/20* (2024.01)
*B08B 3/02* (2006.01)
*B08B 13/00* (2006.01)
*B65G 45/24* (2006.01)

(52) U.S. Cl.
CPC .............. *B08B 1/143* (2024.01); *B08B 1/165* (2024.01); *B08B 1/20* (2024.01); *B08B 3/022* (2013.01); *B08B 3/024* (2013.01); *B08B 13/00* (2013.01); *B65G 45/24* (2013.01); *A61L 2202/17* (2013.01); *B08B 2230/01* (2013.01)

(58) Field of Classification Search
CPC .. B08B 1/20; B08B 1/143; B08B 1/12; B08B 3/022; B08B 3/024; B08B 13/00; B25G 45/24; B25G 45/26; B25G 45/22
USPC .............................. 134/122 R; 198/495; 15/4
See application file for complete search history.

(56) References Cited

U.S. PATENT DOCUMENTS

| | | | |
|---|---|---|---|
| 10,266,348 B1* | 4/2019 | Yoo | ........................ B65G 45/26 |
| 10,954,077 B1* | 3/2021 | Yoo | ........................ B65G 45/22 |
| 2017/0129713 A1 | 5/2017 | Urban | |
| 2019/0084773 A1* | 3/2019 | Handy | ................... B65G 45/22 |

* cited by examiner

SYSTEM FOR CLEANING MODULAR BELTS

CROSS-REFERENCE TO RELATED APPLICATIONS

This application is a continuation under 35 U.S.C. § 371 of International Application No. PCT/MX2019/000038 filed on Apr. 17, 2019 that claims priority to Mexican Application No. MX/a/2019/004329 filed on Apr. 12, 2019. The entire contents of each are incorporated herein by reference.

FIELD OF THE INVENTION

The present invention relates to the mechanical area, in general, it relates in particular to equipment, systems and mechanism for cleaning of elements for materials transport and more specifically to a system for cleaning modular belts.

BACKGROUND OF THE INVENTION

At present, most industrialized production methods are already very efficient or very automated; however, when it is necessary to carry out cleaning work on machinery that has direct contact with the product that is being manufactured, cleaning is still very dependent on manual work, water, detergents and a large work group made up of one or more people depending on the production line.

All the machines that exist at present involve stopping the production line to carry out cleaning by which the product is transported.

At present, most of the equipment with which belt or modular conveyors are cleaned requires all the motors and electrical components to be covered in a plastics material prior to carrying out cleaning tasks, as the large amount of water used for conventional devices or equipment may splash and damage all said components.

As well as stopping production, covering electrical portions with a plastics material and using various cycles of the conveyor to carry out the water-based cleaning, it is sometimes necessary to wait a full operating cycle in order to completely dry the conveyors and be able to restart the production flow.

After carrying out the cleaning with water nozzles or pressure washers, and after drying the surface that was cleaned, solutions or detergents are sprayed to ensure that microbes and bacteria are eliminated.

However, these types of cleaning operations have many drawbacks relating to operations, costs linked to stopping equipment or complete production lines and lost time, effects on electrical equipment associated with the cleaning and washing areas, among many others.

A search was carried out to determine the closest prior art, and the following document was found:

Document D1 U.S. Pat. No. 9,718,626 B2 from Keith Urban, dated 10 Nov. 2016, was found, which discloses a cleaning mechanism for use with a closed-loop conveyor belt supported in a form of continuous movement. The mechanism includes a housing for supporting the belt, a frame mounted to the housing proximate to the belt. A drive shaft extends between spaced apart locations of the frame and includes a pair of head sprockets adapted for supporting the belt at a selected location. A motor is engaged to an input end of the drive shaft. A comb element is pivotally secured to the frame, an upper angled combed edge of the comb element arrayed in spatial non-contacting fashion with a traversing exterior of the belt for capturing remaining debris suspended from the belt. A slave shaft extends between an additional spaced apart location of the frame and which is rotated via a linkage with the drive shaft. The plurality of bristles extend from the slave shaft in a cylindrical arrangement such that selected width extending portions of the bristles are arranged in successive contact with the belt upon rotation of the slave shaft in order to scrub the belt.

One of the main differences between the invention cited and the system according to the present invention is that the invention cited only uses a brush actuated by the motor of the conveyor itself which performs its cleaning function only on the outer face of the belt, being used as a mechanical cleaning method, making it a basic system of very limited scope in terms of cleaning, as it can only remove loose dirt or impurities not adhering to the surface and only a low percentage of adhering and ingrained dirt.

The system according to the invention uses a set of different elements for cleaning both sides of a conveyor belt, said elements being mechanical and chemical elements combined with temperature, for specific time cycles that facilitate and speed up the removal of dirt from modular belts.

The second important difference is that the invention cited (see FIG. 11) has a set of parts (36), (37), (26), (28) which would replace a portion of the original conveyor, making installation thereof complicated on a wide range of conveyors and belts at present on the market.

However, the system according to the present invention may be mounted on the outer structure of any conveyor that is to be cleaned, instead of replacing a portion thereof; specifically designed to be positioned on a return section of a conveyor within a production line, on the lower portion thereof, such that the cleaning task is encapsulated, preventing contamination of the production process in progress and allowing a production process that is underway to continue without stopping production, thus avoiding production downtime.

In addition, the system according to the present invention has the option of being automated so that cleaning cycles are commenced and resources are used according to the conveyor worked on.

Automation consists of turning the different incorporated modules on and off in sequence as well as the option of turning on all said modules simultaneously or only one thereof. The aim is to use only those that produce the cleaning result sought on the surface to be cleaned and not to use extra resources to carry out cleaning that does not require the use of all the modules simultaneously or where the result might be substandard owing to a lack of elements being used to help clean the conveyor.

No document was found that offers all the technical, operational and economic advantages, and those relating to efficiency and effectiveness of the system according to the present invention, which overcomes many drawbacks of the present systems and equipment used for cleaning modular belts.

OBJECTS OF THE INVENTION

The main aim of the invention is to provide a system for cleaning modular belts, designed to be positioned on a return section of a conveyor within a production line, on the lower portion thereof, such that the cleaning task is encapsulated, preventing contamination of the production process in progress and allowing a production process underway to continue without production downtime.

Another object of the invention is to provide said system for cleaning modular belts, which also prevents production downtime during the cleaning cycles and also avoids covering the motors and electrical components with a plastics material prior to carrying out the cleaning tasks, which are required with other equipment and methods where a great deal of water is used.

Another object of the invention is to provide said system for cleaning modular belts which also prevents lost time as it does not require drying and avoids the need to operate the conveyors and equipment without production for cleaning and finally avoids unnecessary waste of energy and at times waiting a complete operating cycle for the conveyors to dry completely and to be able to restart the production flow.

Another object of the invention is to provide said system for cleaning modular belts, which also allows faster cleaning than with manual cleaning (up to 1000 $cm^2$ per minute) and with a 95% saving of water compared with conventional water-based cleaning and owing also to the speed at which the conveyors operate within the industry, thereby avoiding wet floors and the presence of grease on the floor, which also helps reduce the occurrence of accidents.

Another object of the invention is to provide said system for cleaning modular belts wherein the use of dry steam is implemented with different cleaning stations based on physical elements such as brushes, rollers with replaceable cloths, contact scrapers or food-grade detergents to achieve improved cleaning work on the conveyor to be cleaned.

Another object of the invention is to provide said system for cleaning modular belts, which also comprises easy-actuation assembly and mounting elements which facilitates the mounting and dismounting of the cleaning components and elements without the aid of specialized tools, which also allows continuous cleaning, even during production.

All said features and objects will become apparent in the general and detailed description of the present invention supported by the embodiments shown.

BRIEF DESCRIPTION OF THE INVENTION

In general, the system for cleaning modular belts according to the present invention consists of combined work stations mounted on a support structure which may be secured crosswise on the support structure of the modular-belt conveyor, preferably in the return area thereof; said combined work stations are based on four main elements of the cleaning task (physical method, chemical method, thermal method and the contact time of each), which are combined together, and if for some reason said elements have to be reduced or increased, one of the other elements would necessarily have to be changed in proportion in order to achieve the same result; accordingly in the test laboratory said elements were tried out directly on modular conveyors so as to create the best combination of said elements in order to be able to offer a system that is much more efficient for the industry requiring said system.

The elements placed in the system were chosen after the laboratory tests and after evaluating the behavior of the grime and dirt at each of the different stations. The stations may be accommodated in different ways and one of the stations may even be omitted if decided during the use thereof.

The system for cleaning modular belts according to the present invention consists of a support structure configured to be mounted on the structure of a modular-belt conveyor in the return area, without interfering with the operation of the conveyor; a plurality of cleaning stations mounted on said support structure consist of:

a) a first surface cleaning station consisting of at least one roller with microfiber cleaning flaps mounted on a shaft and disposed crosswise on the modular belt, configured to be mounted and dismounted manually and without the use of tools to facilitate the replacement of flap cloths.

b) a cleaning preparation station consisting of at least one transverse duct disposed in an elevated manner on support brackets, with a plurality of ejection nozzles distributed along the length of said at least one duct and along the width of the modular belt in order to sprinkle water in the form of a spray directly on the modular belt, with a temperature and pressure that depend on the accumulation and type of dirt to be removed, with the object of softening the dirt;

c) a pre-cleaning station comprising a system of at least one self-adjustable plastic scraper positioned sloping with an angle of attack above the modular belt and which makes contact therewith over the entire width thereof to remove dirt adhering very closely to the surface of the belt, leaving the surface prepared for cleaning interstices and subsequently for deep cleaning;

d) a second surface cleaning station consisting of at least one pair of rollers with cleaning flaps made of nylon bristles, configured to be mounted and dismounted manually and without the use of tools to facilitate replacement of the bristles due to wear, one being placed on the upper part of the modular belt and one on the lower part thereof for removing the debris adhering most closely to the conveyor. Said rollers of the first and second surface cleaning stations are actuated by a motor and transmission system;

e) a deep-cleaning and sanitization station consisting of a system of dual rotary steam-spraying heads connected to a dry steam generator, preferably a 20 kW/h dry steam generator. The rotary spraying heads rotate at an average speed of 1,300 rpm and spray the steam at a pressure of preferably 10 bar and at a temperature of preferably 180° C., and are positioned at a distance of between 2 cm and 5 cm from the modular belt so as to be able to discharge the steam on the surface and carry out a complete deep cleaning of the modular belt of the conveyor and in turn are able to sanitize the work area as they pass. Excess steam is removed by means of an extractor.

Said rotary spraying heads are mounted on an elevated transverse shaft held by lateral brackets and are actuated by motors.

(f) a station for drying with warm air, formed by at least two air turbines connected to at least one system of air heaters and which take the warm air to an elevated transverse diffuser mounted on brackets which allow a large curtain of warm air of the same width as the conveyor to be generated, with the object of removing the last remaining loosened dirt from the modular belt of the conveyor and the small amount of condensate and water molecules that may be found after the entire cleaning process.

To better understand the features of the present invention the present description has accompanying drawings as an integral part thereof for illustrative but non-limiting purposes, described below.

Figure 1:
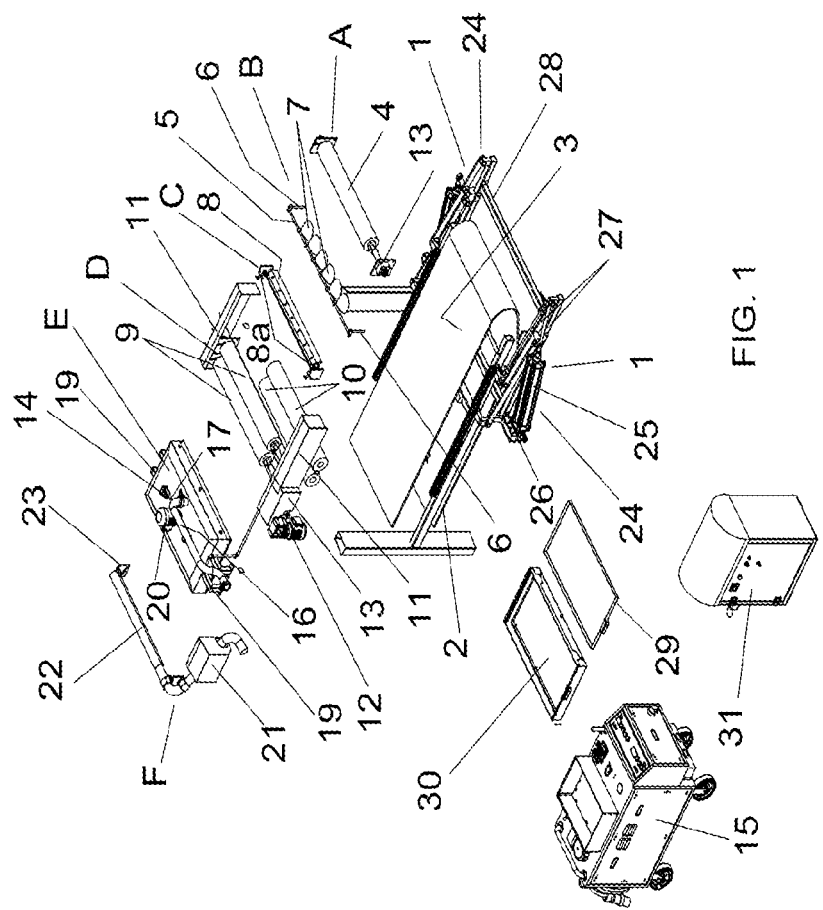
FIG. 1 is an exploded view of the system for cleaning modular belts according to the preferred embodiment of the invention.

For a better understanding of the invention, a detailed description will now be given of one of the embodiments thereof, shown in the drawings accompanying the present description for illustrative but non-limiting purposes.

DETAILED DESCRIPTION OF THE INVENTION

The details characteristic of the system for cleaning modular belts according to the present invention are shown clearly in the description that follows and in the accompanying illustrative drawings, the same reference signs being used to indicate the same parts.

Figure 2:
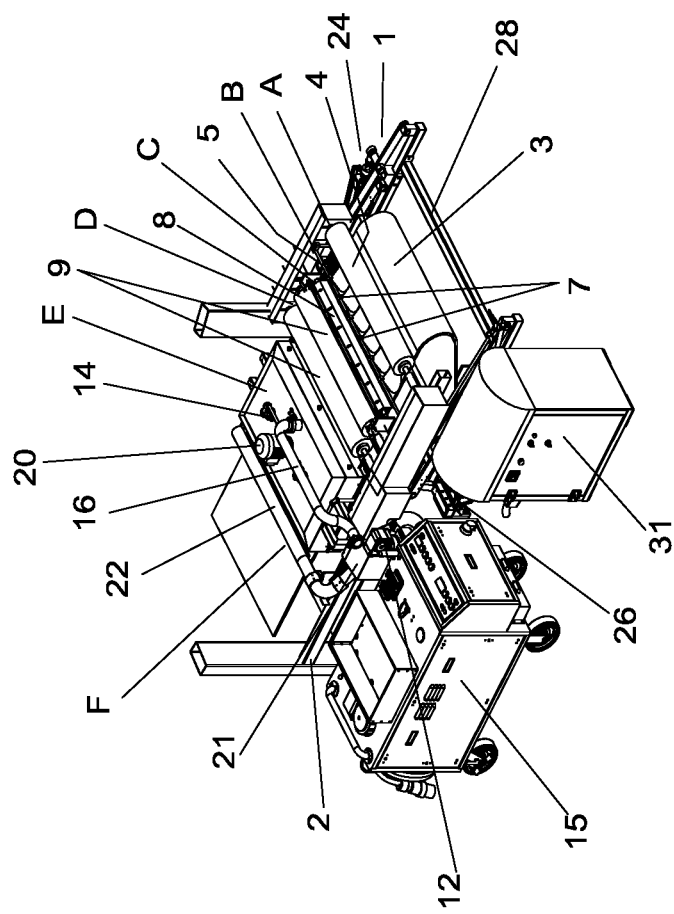
FIG. 2 is a conventional perspective view of the system for cleaning modular belts according to the preferred embodiment of the invention.
Figure 3:
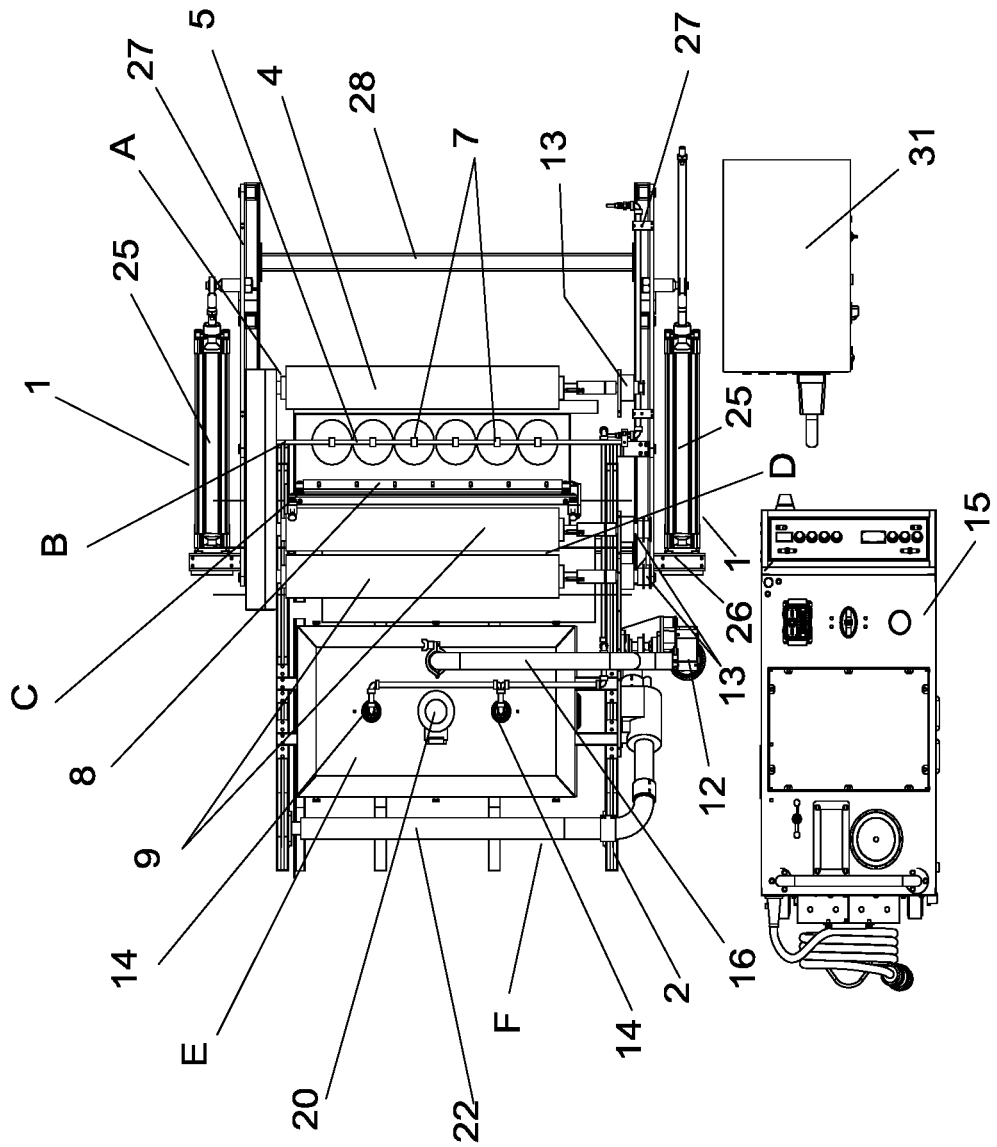
FIG. 3 is a view from above of the system for cleaning modular belts according to the preferred embodiment of the invention.
Figure 4:
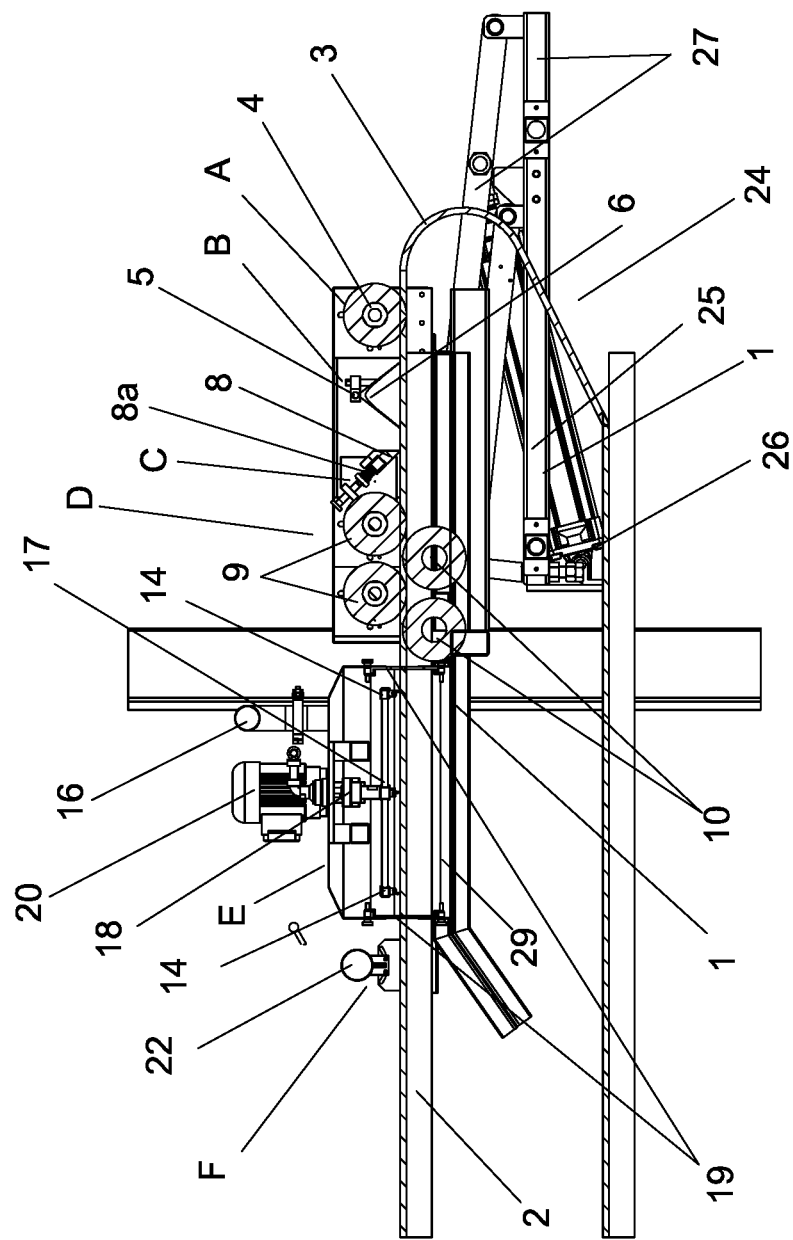
FIG. 4 is a lateral cross section of the system for cleaning modular belts according to the preferred embodiment of the invention.

Referring to FIGS. 1 to 4, the system for cleaning modular belts according to the present invention consists of a support structure (1) configured to be mounted on the support structure (2) of the modular-belt conveyor (3) in the return area, without interfering with the operation of the conveyor; on said support structure (1) are mounted a plurality of cleaning stations, which consist of:

A first surface cleaning station (A) consisting of at least one roller (4) with cleaning flaps preferably made of microfiber, mounted on a shaft and disposed crosswise on the modular belt (3), configured to be mounted and dismounted manually and without the use of tools to facilitate the replacement of the cloth flaps;

A cleaning preparation station (B) consisting of at least one transverse duct (5) disposed in an elevated manner on support brackets (6), with a plurality of ejection nozzles (7) distributed along the length of said at least one duct and along the width of the modular belt in order to sprinkle water in the form of a spray directly on the modular belts (3), with a temperature and pressure that depend on the accumulation and type of dirt to be removed, in order to soften the dirt.

Said system also comprises a pre-cleaning station (C) comprising a system of at least one self-adjustable plastic scraper (8) disposed sloping with an angle of attack above the modular belts (3) and with a cushioning system (8a) and which makes contact therewith over the entire width thereof to remove dirt adhering very closely to the surface of the belt, leaving the surface prepared for cleaning interstices and subsequently for deep cleaning;

A second surface cleaning station (D) consisting of two pairs of rollers (9, 10) with cleaning flaps made of nylon bristles, configured to be mounted and dismounted manually on a lateral support structure (11) and without the use of tools, to facilitate the replacement of the bristles due to wear, one pair of rollers (9) being placed on the upper part and one pair of rollers (10) on the lower part of the modular belts (3) to remove the debris adhering most closely to the conveyor. Said rollers (4, 9 and 10) of the first and second surface cleaning stations are actuated by a motor (12) and transmission system (13).

A deep-cleaning and sanitization station (E) consisting of a system of dual rotary steam-spraying heads (14) connected to a dry steam generator (15), preferably a 20 kW/h dry steam generator. The rotary spraying heads (14) rotate at an average speed of 1,300 rpm and spray steam at a pressure preferably of 10 bar and a temperature of preferably 180° C., and are positioned at a distance of between 2 cm and 5 cm from the modular belts (3) so as to be able to discharge the steam on the surface and carry out a complete deep cleaning of the modular belts (3) of the conveyor and in turn are able to sanitize the work area as they pass. Excess steam is removed by means of an extractor (16).

Said rotary spray heads (14) are mounted on an elevated transverse shaft (17) with a drive mechanism (18), which produces and transmits the movement to the helices through which the steam passes and is held by side brackets (19) and are actuated by motors (20).

A station for drying (F) with warm air, formed by at least two air turbines (not shown) connected to at least one system of air heaters (21) and which take the warm air towards an elevated transverse diffusor (22) mounted on brackets (23) which allow a large curtain of warm air to be generated of the same width as the conveyor, in order to remove the last remaining loosened dirt from the modular belts (3) of the conveyor and the small amount of condensate and water molecules that may be found after the entire cleaning process.

Said support structure (1) comprises on each side of the conveyor an elevation mechanism (24) defined by an actuator (25) recessed in an assembly (26) secured to the support structure (2). The end of said actuator (25) is secured pivoting on a pair of articulated struts (27) connected to a transverse bar (28) on which the components beneath the modular belts (3) are mounted to adjust the position thereof. Said elevation mechanism (24) also allows the cleaning system to be mounted and dismounted from the support structure (2). The mechanism is independent of the cleaning system as the design and operation thereof may vary widely depending on the available space for each conveyor to be cleaned.

Said support structure (1) also comprises a platform (29) beneath the modular belts (3) configured to receive and support trays for collecting debris from the cleaning (30).

The system also includes a control module (31) where the actuation and cut-off elements for the different cleaning stations are bought.

The invention has been described sufficiently for a person having average skill in the art to be able to reproduce and obtain the results mentioned in the present invention. However, any person skilled in the art relating to the field in which the present invention competes may be capable of making modifications that have not been described in the present application. However, if in applying said modifications to a particular structure or to the manufacturing process thereof the subject matter claimed in the following claims is required, said structures should be considered to fall within the scope of the invention.

We claim:

1. A system for cleaning modular belts, consisting of a support structure configured to be mounted and dismounted in a return area from a modular-belt conveyor, consisting of a modular belt having an upper and a lower surface, wherein a plurality of independently-operating cleaning stations are mounted on said support structure and further wherein said plurality of cleaning stations, consisting of:
 a) a first surface cleaning station consisting of at least one roller with affixed cleaning flaps disposed crosswise on the modular belt;
 b) a cleaning preparation station consisting of at least one transverse duct elevated on support brackets, wherein a plurality of ejection nozzles are distributed along length of said at least one traverse duct and along entire width of the modular belt in order to spray water directly on the modular belt;
 c) a pre-cleaning station comprising a system of one or more self-adjustable plastic scrapers positioned at an angle above the modular belt, wherein said one or more self-adjustable plastic scrapers are situated to contact the entire width of the modular belt so as to scrape off dirt and debris adhered to the upper surface of the modular belt located below the at least one or more self-adjustable plastic scrapers;
 d) a second surface cleaning station consisting of one or more pairs of rollers having one or more cleaning flaps, a first roller of a pair of rollers having one or more cleaning flaps affixed to en the upper surface of the modular belt and a second roller of a pair of rollers having one or more cleaning flaps affixed to en4 the lower surface of the modular belt, wherein the cleaning flaps on the pair of rollers remove dirt and debris adhered to the modular-belt conveyor; wherein said one or more pairs of rollers of the first and second surface cleaning stations are actuated by a motor and transmission system;
 e) a deep-cleaning and sanitization station consisting of a plurality of rotary steam-spraying heads connected to a dry steam generator; wherein said rotary spraying heads are mounted on an elevated transverse shaft held by lateral brackets and are actuated by at least one motor; and
 f) a station for drying with heated air comprising two or more air turbines connected to one or more air heaters that supply the heated air to an elevated transverse diffuser mounted on brackets wherein the heated air dries an entirety of the modular-belt conveyor.

2. The system of claim 1, wherein the cleaning flaps comprise nylon bristles or nylon microfibers.

3. The system of claim 1, wherein said rollers of the first and second surface cleaning stations are configured to be mounted and dismounted manually without tools.

4. The system of claim 1, wherein said dry steam generator works at 20 kiloWatts per hour (kW/h) and said plurality of rotary steam-spraying heads rotate at an average speed of 1,300 revolutions per minute (rpm) sprayings team at a pressure of 10 bars and at a temperature of 180° C.

5. The system of claim 1, wherein said plurality of rotary steam-spraying heads are positioned at a distance of between 2 cm and 5 cm from the modular belt.

6. The system claim 1, wherein excess steam generated at the deep-cleaning and sanitization station is removed using a steam extractor.

7. The system of claim 1, wherein said one or more self-adjustable plastic scrapers positioned sloping with an angle above the modular belt, comprises a cushioning system that contacts the scrapers with the modular belt.

8. The system of claim 1, wherein said support structure comprises two elevation mechanisms defined by actuators recessed in an assembly secured to the conveyor; the actuators are pivotally secured on a pair of articulated struts connected to a transverse bar to adjust the position of the support structure.

9. The system of claim 1, wherein said support structure further comprises a platform situated beneath the modular belt configured to receive and support trays for collecting dirt and debris from a cleaning of the modular belt.

10. The system of claim 1, further comprising a control module.

11. The system of claim 1, wherein said cleaning stations are accommodated randomly.

* * * * *